(12) United States Patent
Zollinger (10) Patent No.: US 8,074,528 B2
(45) Date of Patent: Dec. 13, 2011

(54) IN-LINE VALVE SAMPLING SYSTEM

(75) Inventor: Peter Zollinger, Aathal (CH)

(73) Assignee: Neotecha AG, Hombrechtikon (CH)

( * ) Notice: Subject to any disclaimer, the term of this patent is extended or adjusted under 35 U.S.C. 154(b) by 768 days.

(21) Appl. No.: 12/169,316

(22) Filed: Jul. 8, 2008

(65) Prior Publication Data

US 2009/0013805 A1     Jan. 15, 2009

(30) Foreign Application Priority Data

Jul. 11, 2007    (EP) ..................................... 07252769

(51) Int. Cl.
     *G01N 1/00*      (2006.01)
(52) U.S. Cl. .................................................. 73/863.86
(58) Field of Classification Search ................ 73/863.86
See application file for complete search history.

(56) References Cited

U.S. PATENT DOCUMENTS

| | | | | | |
|---|---|---|---|---|---|
| 2,736,201 | A | * | 2/1956 | Ohlsen et al. | 73/863.86 |
| 4,344,453 | A | * | 8/1982 | Tuchenhagen et al. | 137/240 |
| 4,458,543 | A | * | 7/1984 | Mieth | 73/863.86 |
| 4,516,752 | A | * | 5/1985 | Babbitt et al. | 251/214 |
| 4,580,452 | A | * | 4/1986 | Masson | 73/863.86 |
| 5,263,682 | A | * | 11/1993 | Covert et al. | 251/214 |
| 5,357,995 | A | * | 10/1994 | King et al. | 73/863.86 |
| 5,370,146 | A | * | 12/1994 | King et al. | 73/863.86 |

* cited by examiner

*Primary Examiner* — Hezron E Williams
*Assistant Examiner* — Nashmiya Fayyaz (57) ABSTRACT

An in-line valve sampling system connected to a pipe conduit extracts a sample of process media in a receiving container or receptacle for testing. The valve sampling system provides a resilient sealing mechanism for corrosive process media at elevated and fluctuating temperature ranges by providing a packing cartridge having a thin film of PTFE material biased by at least one O-ring to provide a seal between a valve spindle and a raised portion of the packing cartridge.

19 Claims, 8 Drawing Sheets

IN-LINE VALVE SAMPLING SYSTEM

FIELD OF THE INVENTION

The present invention relates generally to valves. More particularly, the invention relates to an in-line valve sampling system connected to a pipe conduit which extracts a sample of process media in a receiving container or receptacle for testing. The valve sampling system provides a resilient sealing mechanism for corrosive or abrasive process media at elevated and fluctuating temperature ranges.

BACKGROUND OF THE INVENTION

Sampling devices are used in various applications such as the chemical, food, pharmaceutical and energy industries to collect a sample of process media for testing and/or analysis. These sampling devices are usually in the form of a valve that when opened is capable of extracting liquids, gases or other process media from an attached pipeline or conduit. Some types of sampling devices require process interruption where the system is temporarily shut down and a representative sample is taken. Various types of process media may be sampled including water, fuel, beverages as well as toxic substances. Danger of harmful spills is not present when innocuous media is sampled. However, when dangerous or expensive media is sampled, spillage and waste become problematic.

Certain sampling devices permit the removal of sampling media from a conduit into a receptacle via a connection pipe or tube. When corrosive or abrasive material is being sampled, this environment allows for the corrosive effects of the material to compromise the integrity of the system. This limits the number of strokes or cycles in the life of the valve. In addition, when the process media is corrosive material, the valve utilized in the sampling system also becomes susceptible to corrosion. This condition is exasperated when the system undergoes temperature elevations and fluctuations.

Various types of configurations may be employed to try and limit the corrosive effects on the operation of the valve. One configuration utilizes a lining on the valve spindle with a fully fluorinated Fluoropolymer like Teflon® and a Teflon® seal. The Teflon® materials referred to herein are fully fluorinated fluoropolymers including, but not limited to PTFE, PFA, TFM or NXT. However, this makes it difficult to achieve a perfect seal because of the thermal expansion of the Teflon® material due to elevated or fluctuating temperatures. In addition, the Teflon® to Teflon® seal creates unwanted wear resulting from the linear movement of the spindle. Accordingly, there is a need for a valve sampling system that accommodates adequate sealing characteristics in a corrosive process media environment at elevated and fluctuating temperatures. The above-referenced drawbacks and others are overcome by the present invention described herein with reference to the detailed description, drawings and appended claims.

SUMMARY OF THE INVENTION

Embodiments of the invention are directed to a sampling system that includes a valve unit installed in a process pipeline for receiving a sample of process media flowing through the pipeline. The sampling device includes a valve unit body configured to house the valve unit which has a valve port. In an open position, the valve port supplies the sample of process media and in its closed position, prevents the sample of process media from being extracted from the pipeline. A valve spindle is disposed within the valve unit body and is lined with PTFE. The valve spindle includes a head portion and is spring biased in the closed position such that the head portion creates a seal with the valve port. An operating lever is connected to the valve spindle and has a range of motion from the open position to the closed position. A packing cartridge is positioned around the valve spindle and has a first cut-out portion and an inner wall. The inner wall is lined with PTFE and is in contact with the valve spindle. The cartridge receives an O-ring which exerts a sealing force between the valve unit body and the spindle to prevent unwanted process flow from entering the valve unit body. A receptacle is connected to the valve unit body and is configured to receive the sample media.

DESCRIPTION OF THE EMBODIMENTS

Figure 1:
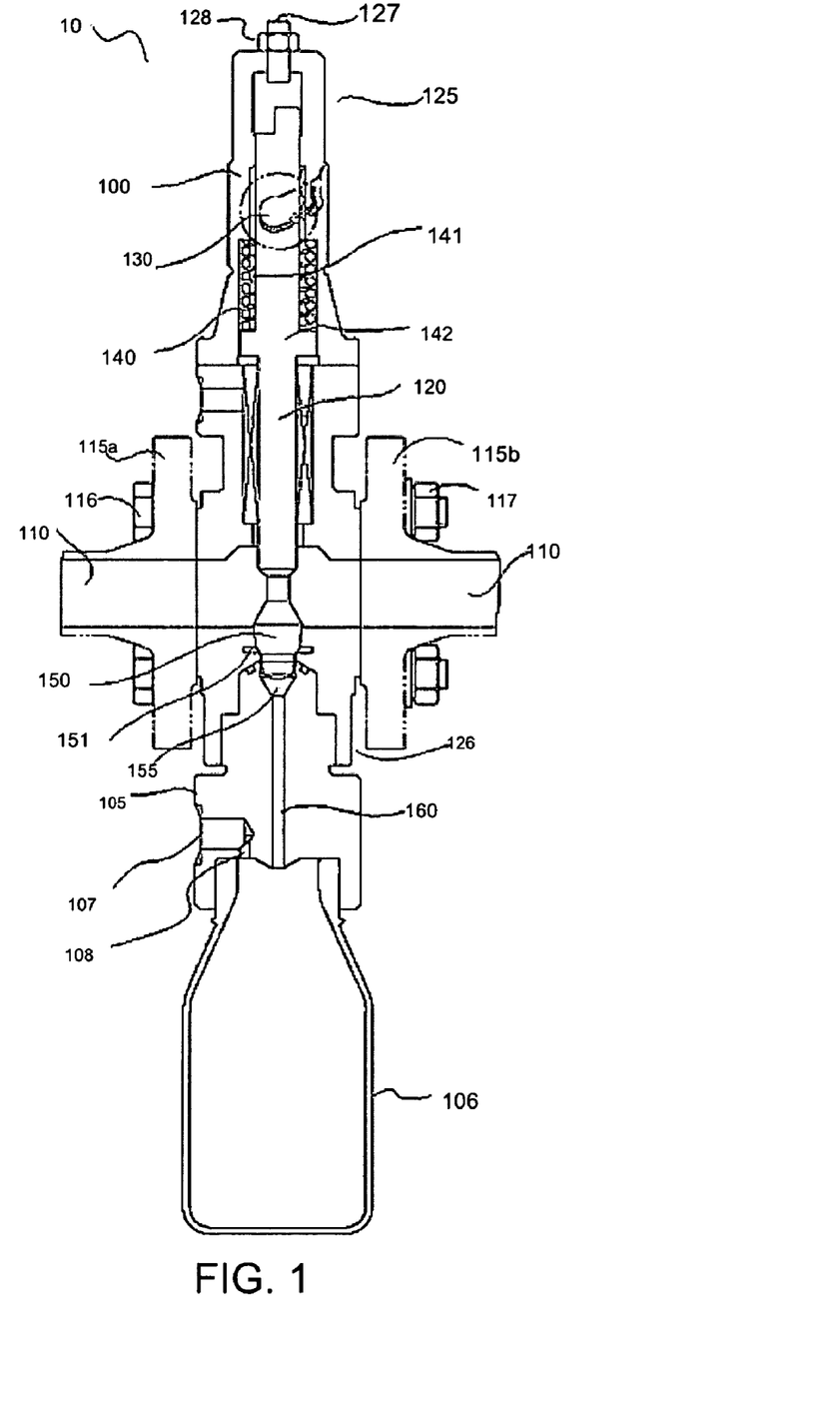
FIG. 1 illustrates a simplified profile view of a closed valve sampling system in accordance with an embodiment of the present invention.

FIG. 1 illustrates an exemplary embodiment of a sampling system 10 having a valve unit body 100 and a receiving or sampling unit 105 installed directly into a process pipeline 110. Sampling system 10 may be attached to pipeline 110 via valve flanges 115a and 115b. Valve flanges 115a and 115b are the type typically used in valve conduit connections having a plurality of bolts or connectors 116 and retaining nuts 117 spaced around the circumference of flanges 115a and 115b. Valve body 100 includes set screw 127 and hex nut 128 and is positioned along the process flow axis of process pipeline 110. Sampling unit 105 may include, for example, a receptacle or bottle 106 for receiving the sample which is detachably connected from valve unit body 100. Sampling unit 105 also includes a vent 107 for discharging air from bottle 106 when the bottle is filled. Bottle 106 may be, for example standard Glass, PFA or stainless steel with an ISO GL 45 thread to vent 107 via a ¼ inch NPT connection to port 108. Alternatively, a syringe collection receptacle (as described below) may also be employed depending on the process media being sampled as well as the various safety and contamination factors associated with the sampling media.

A valve spindle 120 is centrally disposed within valve unit body 100 and extends from a top portion 125 to a lower portion 126. Spindle 120 may be, for example, PFA encapsulated stainless steel secured within valve unit body 100. Spindle 120 includes a contoured spindle head portion 150 which engages seat sample port 155 when valve unit 100 is in a closed position. Spring coil 140 biases spindle 120 to form a seal between spindle head portion 150 and sample port 155. Sample port 155 is connected to sampling channel 160 which extends into bottle 106 and provides a path for the deposit of sampling media from process pipeline 110 to sampling container or bottle 106. Spindle head portion 150 has a cone configuration, but other shapes may be employed to provide a seal with sample port 155 via seat 151 to prevent process media from flowing into channel 160 when valve unit 100 is in a closed position.

Figure 2:
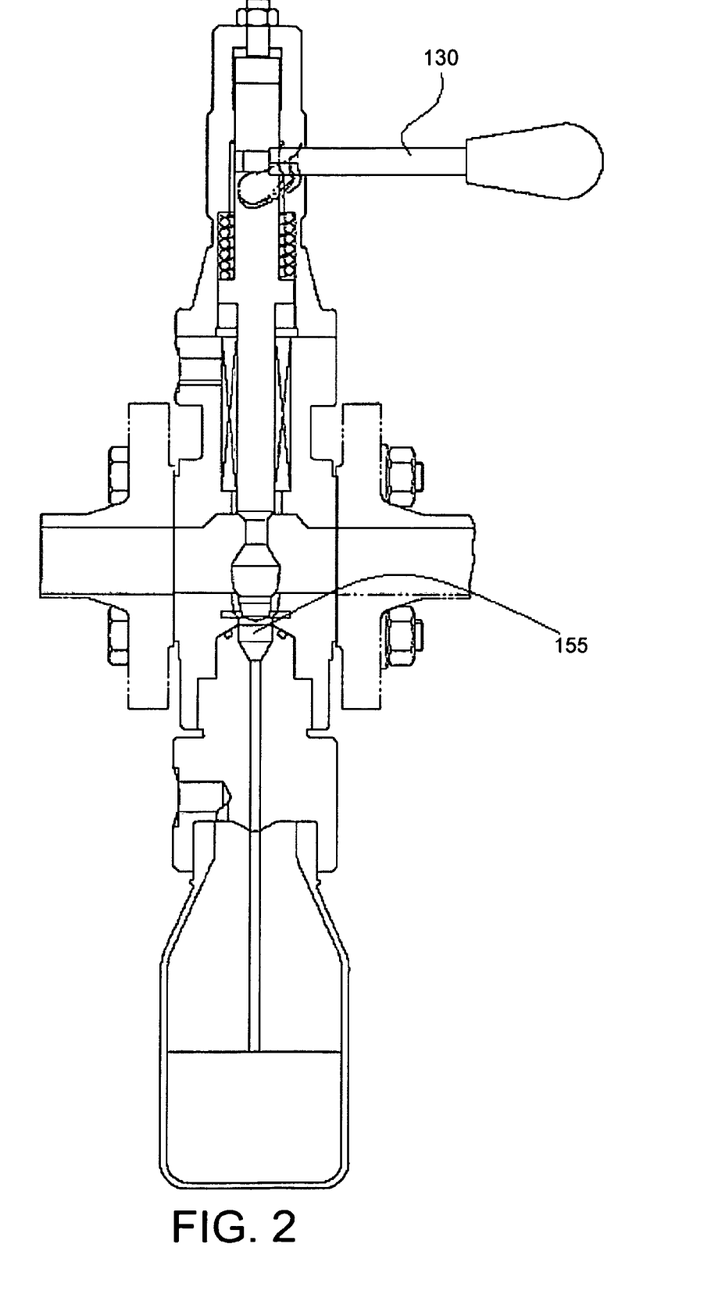
FIG. 2 illustrates a simplified profile view of an open valve sampling system shown in FIG. 1 in accordance with an embodiment of the present invention.

FIG. 2 illustrates sampling system 100 in an open position. Stroke or operating lever 130 (shown in phantom in FIG. 1) is fixedly connected to spindle 120 and activated when sampling process media is to be deposited in bottle 106 from pipeline 110. Operating lever 130 extends a distance away from valve unit body 100 and may include handle portion 131 for ease and safe of operator use. When operating lever 130 is rotated anti-clockwise for activation, spindle 120 moves upward within valve body 100. As spindle 120 is displaced upward, spindle head portion 150 is unseated from seat 151 opening sample port 155 to allow process media to flow from pipeline 110 into bottle 106 via channel 160. As spindle 120 moves upward, coil spring 140 positioned in spring support cavity 141 of valve body 100 is compressed via spring cam portion 142 providing a downward bias against spindle 120. Operating lever 130 is spring loaded and activated by linear movement, for example 90° anti-clockwise, by coil spring 140 which forces spindle 120 into a closed position when lever 130 is released (referred to as a "dead man lever"). To prevent unwanted activation, operating lever 130 may be locked. The stroke of lever 130 may be adjusted with stud 127 and nut 128 to regulate the speed at which sampling media fills receptacle 106. When sampling media, it must be guaranteed that samples are tapped from pipeline 110 and filled in bottle 106 in a way that neither the contents of the pipeline nor the sample get into contact with the outside air or with any alien matter. In addition, when removing bottle collector 106 at the end of the sampling process, the detachment mechanism for bottle 106 must be such as to prevent the spilling or escape of the sample.

Packing, an essential part of any valve, wraps around spindle 120 to ensure smooth vertical displacement within valve unit body 100 and provides a seal to prevent process leakage. As stated earlier, spindle 120 is stainless steel wrapped in Teflon® PFA. In certain corrosive environments, the sealing material is also Teflon® PFA which results in a Teflon® to Teflon® seal. This sealing configuration is sometimes necessary to satisfy emissions standards unique to particular countries especially in highly corrosive applications. For example, the German administrative regulation TA Luft and the VDI 2440 emission standard test requires less than 1 ppm leakage through the valve stem for valve emissions in certain process industries. Thus, the combination of linear movement of a Teflon® wrapped spindle 120 within valve body 100 with a Teflon® seal makes it difficult to achieve the necessary sealing requirements at elevated and fluctuating temperatures to satisfy stringent emissions standards. Temperature fluctuations are within the range of −20° C. to 200° C. This is mainly due to the fact that as the temperature inside the valve unit increases, the Teflon is heated and expands because of it's the high thermal expansion properties. Additionally, during the cold flow process, the seal between the packing and spindle may be altered.

Figure 3:
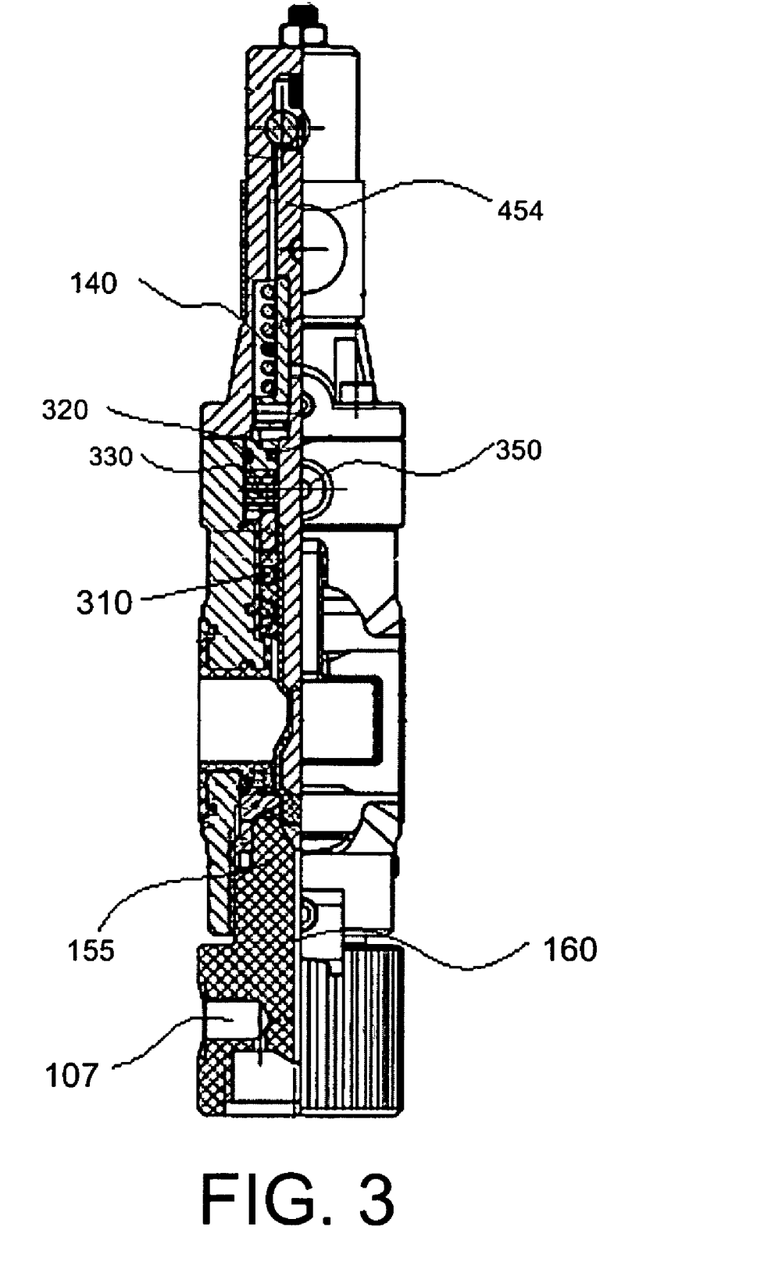
FIG. 3 is a cut-away cross-sectional view of the valve sampling system in accordance with an embodiment of the present invention.

FIG. 3 is a detailed cross sectional cut-away view of the sampling system unit 10 shown in FIGS. 1 and 2. Spindle 120 disposed within valve unit body 100 is biased in a downward direction by coil spring 140. As described above, when the valve is opened, spindle 120 moves upward releasing spindle head portion 150 from seat 151. This allows process media from pipeline 110 to enter sampling channel 160 via sample port 155. Primary spindle seal 310 is positioned above the pipeline 110 connection and serves to create a seal between spindle 120 and valve body unit 100. Primary seal 310 creates a horizontal force against spindle 120 to maintain the sealing arrangement at elevated and fluctuating temperatures. Secondary spindle seal 320 is disposed vertically between coil spring 140 and primary seal 310. Belleville washer 330 is vertically disposed between secondary seal 320 and primary seal 310. Vent port 350 is located between primary seal 310 and secondary seal 320 to allow connection for a vent pipe (not shown) for releasing permeation through the valve unit or to connect a leak detection device.

Figure 4:
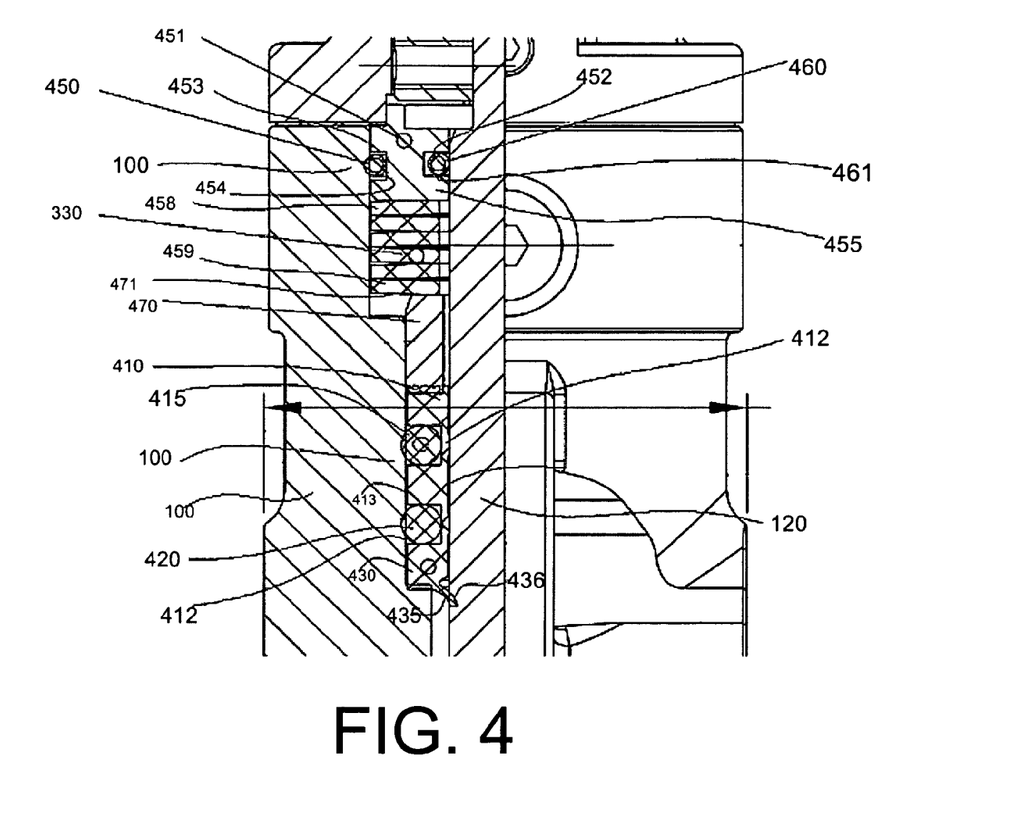
FIG. 4 is a cut-away cross-sectional view of the sealing areas of the valve sampling system in accordance with an embodiment of the present invention.

FIG. 4 is a cut-away cross-sectional view of the primary seal area 310 and secondary seal area 320 of sampling system unit 10. Primary seal area 310 includes a cartridge 410, first O-ring 415, second O-ring 420 and lip portion 430. Cartridge 410 may be, for example TFM™, a trademarked name of Dyneon, a 3M Company or NTX, a trademark name of DuPont, which are modified polytetrafluoroethylene (PTFE) fluoroplastic material that maintains chemical and heat resistance properties of conventional PTFE with lower melt viscosity. Cartridge 410 includes interior wall 412 and cut-out portions 411 and 413. First O-ring 415 is positioned within first cut-out portion 411 and is disposed between cartridge wall 412 and valve unit body 100. Second O-ring 420 is positioned within second cut-out portion 413 and is disposed between cartridge wall 412 and valve unit body 100. Because wall portion 121 of spindle 120 and wall portion 412 of cartridge 410 are lined with Teflon, corrosive wear may result from the linear movement of spindle 120 thereby compromising the sealing properties of the valve unit. By positioning O-rings 415 and 420 around spindle 120, a force is exerted between valve unit body 100 and spindle 120 to maintain the seal between spindle 120 and interior cartridge wall 412. Although O-rings 415 and 420 are shown as overlapping valve unit body, when installed the O-rings are compressed into position to provide the necessary forces against spindle 120 to create the above-described seal. Lip portion 430 of cartridge 410 is disposed below second cut out portion 413 and extension arm 435. Extension arm 435 downward curved radius and is used to wipe away hard particles when spindle 120 is lifted within valve unit body 100. This prevents any hard particles from entering the sealing area between spindle 120 and cartridge wall 412 which may compromise the seal. As shown, extension arm 435 overlaps spindle 120, but when installed provides contact between spindle 120 and side 436 of extension arm 435.

Secondary seal area 320 includes L-ring 451 having a first cut-out portion 452 and second cut-out portion 453. First cut-out portion 452 includes interior wall 461 and houses O-ring 460. Second cut-out portion 453 includes interior wall 454 and houses O-ring 450. A force in direction A is exerted against spindle 120 by O-rings 450 and 460. Although O-ring 450 is shown as overlapping valve unit body 100 and a space is shown between O-ring 460 and interior wall 461. However, when installed O-rings 450 and 460 compress creating a seal between L-ring 451 and spindle 120. Belleville washer 330 is disposed between L-ring 451 and spacer 470. In particular, a first end 458 of Belleville washer 330 contacts lower portion 455 of L-ring 451. Second end 459 of Belleville washer 330 contacts an upper wall 471 of spacer 470. As fluctuations in temperature changes the dimensions of PTFE, Belleville washer 330 allows for this expansion through vertical compression within valve unit body 100.

Figure 5:
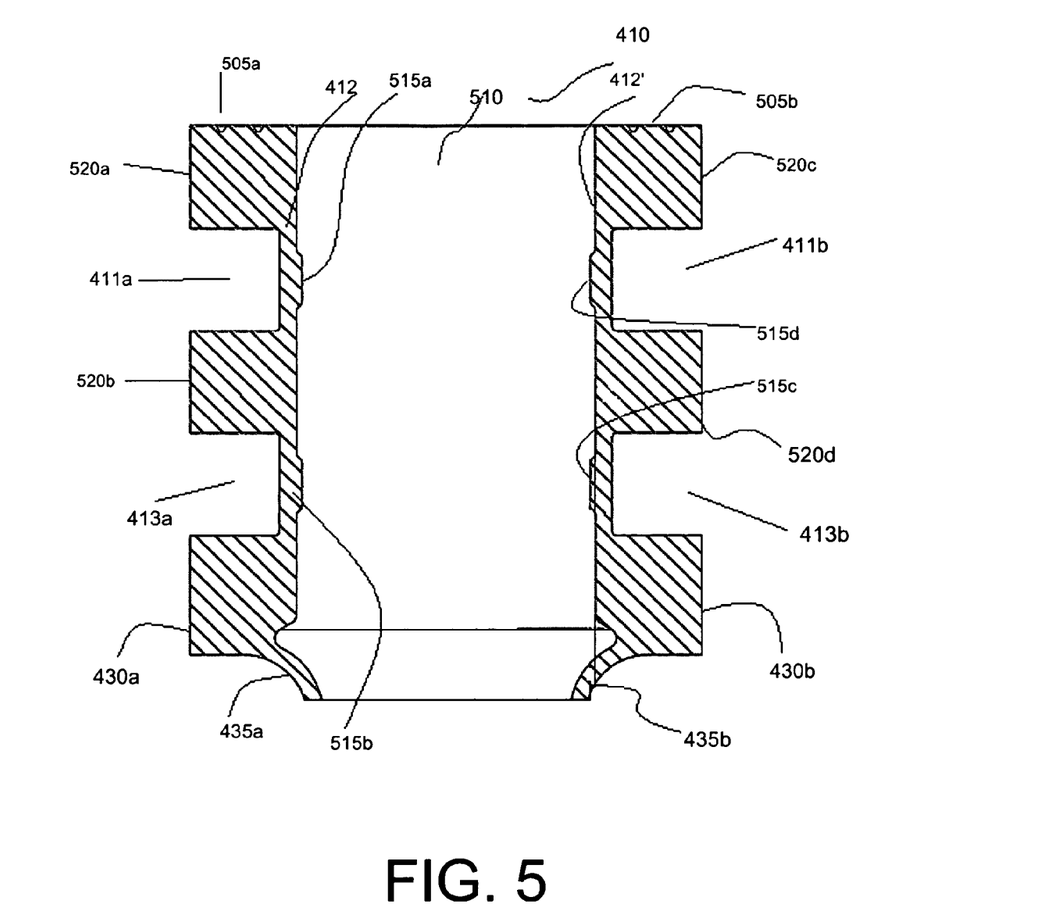
FIG. 5 illustrates a packing cartridge utilized in the valve sampling system in accordance with an embodiment of the present invention.

FIG. 5 illustrates a cross-sectional view of packing cartridge 410. When cartridge 410 is preloaded in valve unit body 100, it surrounds spindle 120 thereby creating a perimeter seal. It is understood that cartridge 410 is a unitary valve member that is preloaded into valve unit body 100 with a centrally disposed channel 510 which receives spindle 120. For ease of explanation, the cartridge is being described herein as having a first half and a second half. Cartridge 410 includes a first half 505a and a second half 505b with a channel 510 disposed there through. Channel 510 is configured to receive spindle 120 as primary sealing area 310. First half 505a includes raised portions 520a, 520b, cut-out portions 411a and 413a and lip portion 430a. Similarly, second half 505b includes raised portions 520c, 520d, cut-out portions 411b, 413b and lip portion 430b. First half 505a has a common interior wall 412 which extends from raised portion 520a through to lip portion 430a. Likewise, second half 505b has a common interior wall 412' which extends from raised portion 520c through to lip portion 430b. Each of the cut-out portions 411a, 411b, 413a and 413b each are configured to receive an O-ring. For example, cut-out portion 411a receives O ring 415 disposed between interior wall 412 and valve unit body 100. Cut-out portion 413a receives O-ring 420 disposed between interior wall 412 and valve unit body 100. Cut-out portion 411b receives an O-ring (not shown) disposed between interior wall 412' and valve unit body 100. Cut-out portion 413b receives an O-ring (not shown) disposed between interior wall 412' and valve unit body 100. It should be understood that the O-ring disposed in cut-out portions 411a and 411b is the same O-ring as it extends around spindle 120. Similarly, the O-ring disposed within cut-out portions 413a and 413b is the same O-ring as it extends around spindle 120. As described above, lip portion 430a includes extension arm 435a and lip portion 430b includes extension arm 435b.

The interior walls 412, 412' of cartridge 410 have raised rings 515a, 515b, 515c and 515d. Raised ring 515a corresponds to cut-out portion 411a and raised ring 515b corresponds to cut-out portion 413a. Similarly, raised ring 515c corresponds to cut-out portion 413b and raised ring 515d corresponds to cut-out portion 411b. It should be understood that cut-out portions 411a and 411b are the same cut-out portions because the border configuration of cartridge 410 arranged around spindle 120. Likewise, cut-out portions 413a and 413b are the same cut-out portions because the border configuration of cartridge 410 arranged around spindle 120. Wall 412 and 412' at raised rings 515a, 515b, 515c and 515 have a thickness of approximately 1 mm. The primary seal 310 occurs along the raised rings 515a, 515b, 515c and 515d and spindle 120. The O-rings 415 and 420 exerts the force to compress the Teflon lined raised rings against Teflon coated spindle 120. Because the area (raised rings 515a, 515b, 515c and 515d) where the primary seal actually occurs is relatively thin, O-rings 415 and 420 exert a sufficient force around spindle 120 to create a seal and prevent unwanted media from emanating from pipeline 110 when spindle 120 moves linearly within valve unit body 100. In this manner, cartridge 410 provides a preloaded stuffing box with the use of a pair of O-rings to provide a resilient and reliable Teflon to Teflon seal between valve unit body 100 and spindle 120 which can withstand elevated and fluctuating process temperatures.

Figure 6:
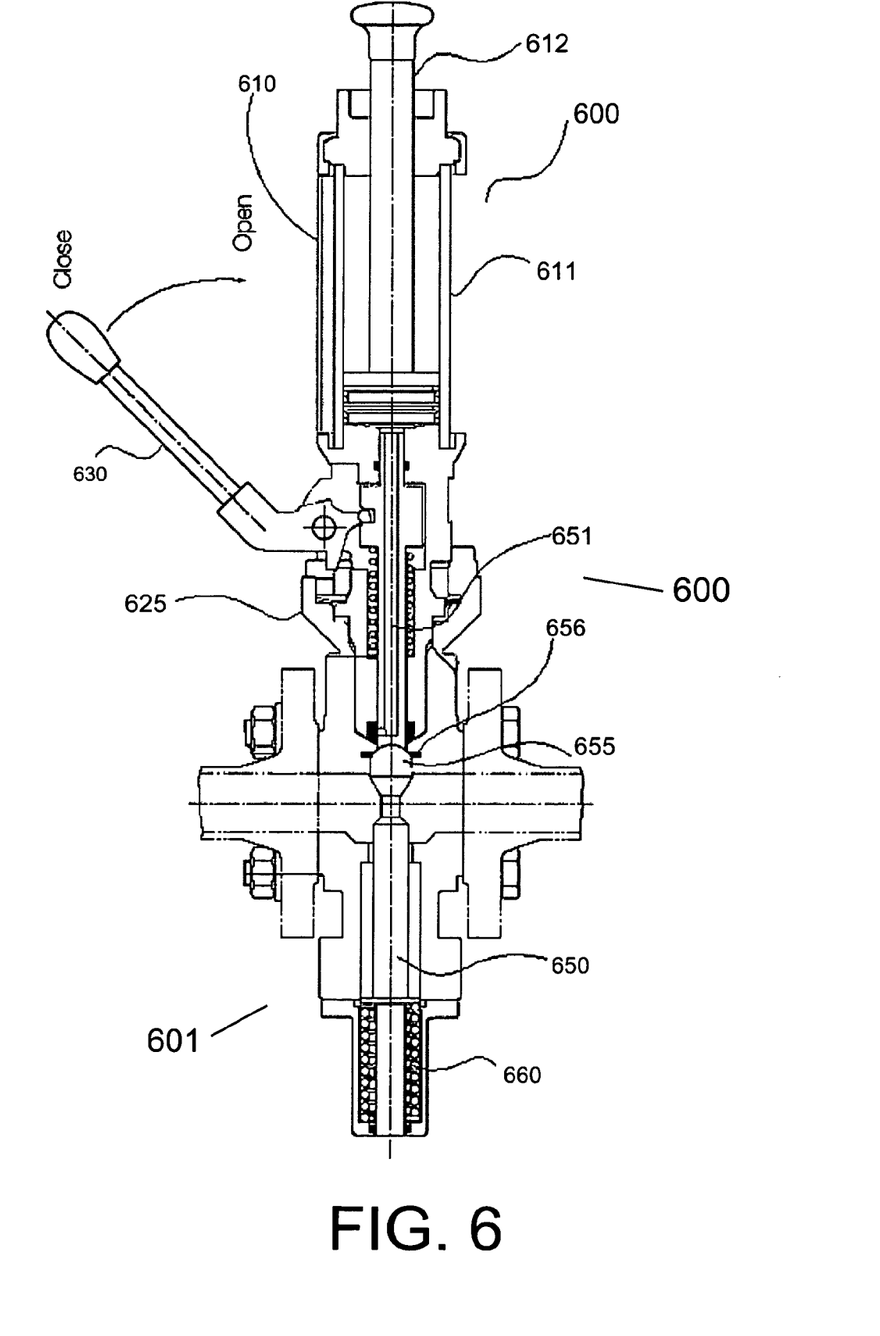
FIG. 6 illustrates an alternative embodiment of the present invention where the receptacle portion of the valve sampling system is a syringe.

FIG. 6 illustrates an alternative embodiment of the present invention where the receptacle portion of valve 601 is syringe 610. This type of sampling device is utilized when total containment of sampling media is necessary. The connection of syringe 610 to valve body 620 may be, for example, using a universal bayonet type adapter 625. Again, valve sampling system 600 is positioned within process pipeline 110 and valve 601 is opened via operator lever 107. Syringe 610 includes cylinder 611 and piston 612. Sampling system 600 includes valve spindle 650 and syringe spindle 651. Operator lever 630 is connected to syringe spindle 651. In its closed position as shown in FIG. 6, spindle head 655 engages seat 656. Spindle 650 is biased in this closed position by coil spring 660 similar to spring coil 140 of the embodiment shown in FIGS. 1-4.

Figure 7:
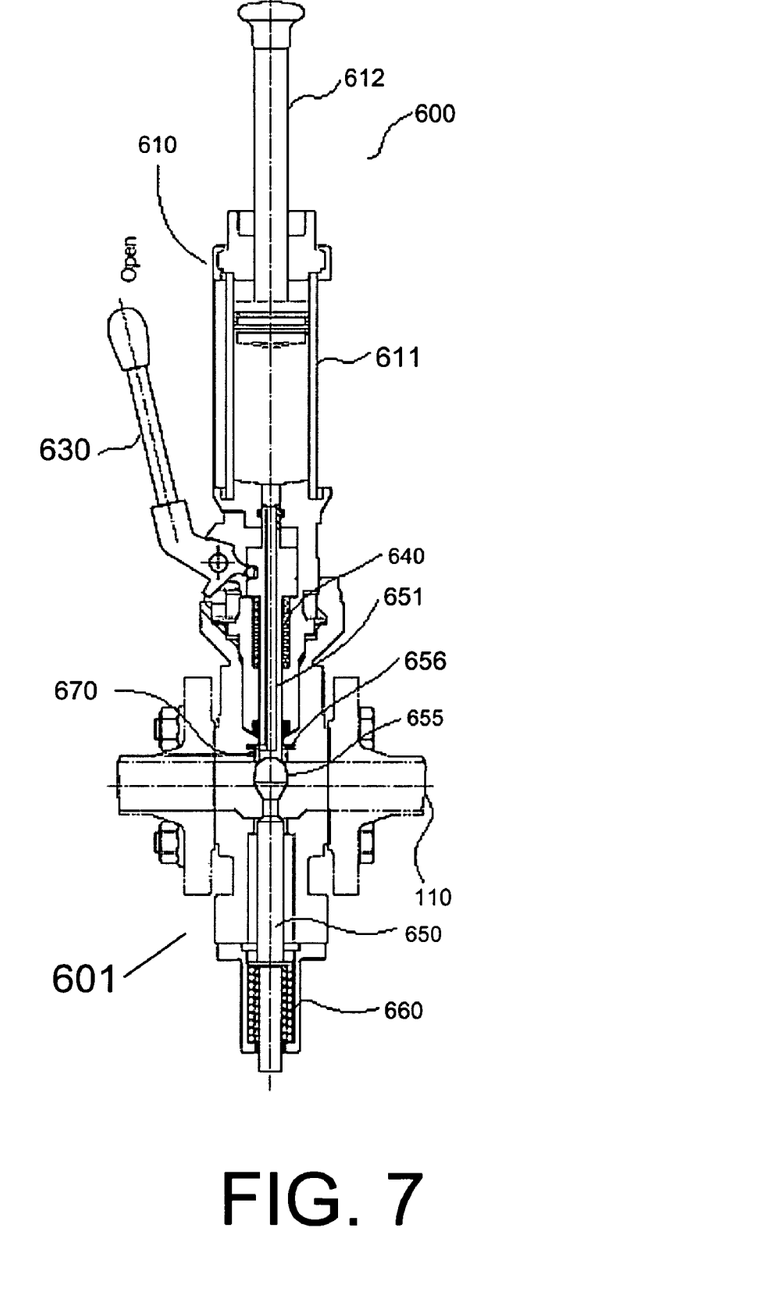
FIG. 7 illustrates the syringe configuration shown in FIG. 6 in an open position.

FIG. 7 illustrates the syringe configuration sampling system 600 in an open position. When operating lever 630 is displaced to the open position, syringe spindle 651 forces valve spindle 650 from seat 656, thus opening valve 601 such that spindle head 655 disengages from seat 656. This allows process media to enter through port 670 into cylinder 611 of syringe 610. If sampling system 600 is under pressure, the sample will flow into cylinder 611 of syringe 610 displacing piston 612. If the sampling system 600 is in a vacuum, the sample has to be pulled from pipeline 110 into cylinder 611 by pulling piston 612 away from pipeline 110. When operating lever 630 is released, spring 640 biases syringe spindle 651 back toward its closed position which forces coil spring 660 to displace valve spindle 650 such that spindle head 655 engages seat 656.

Figure 8:
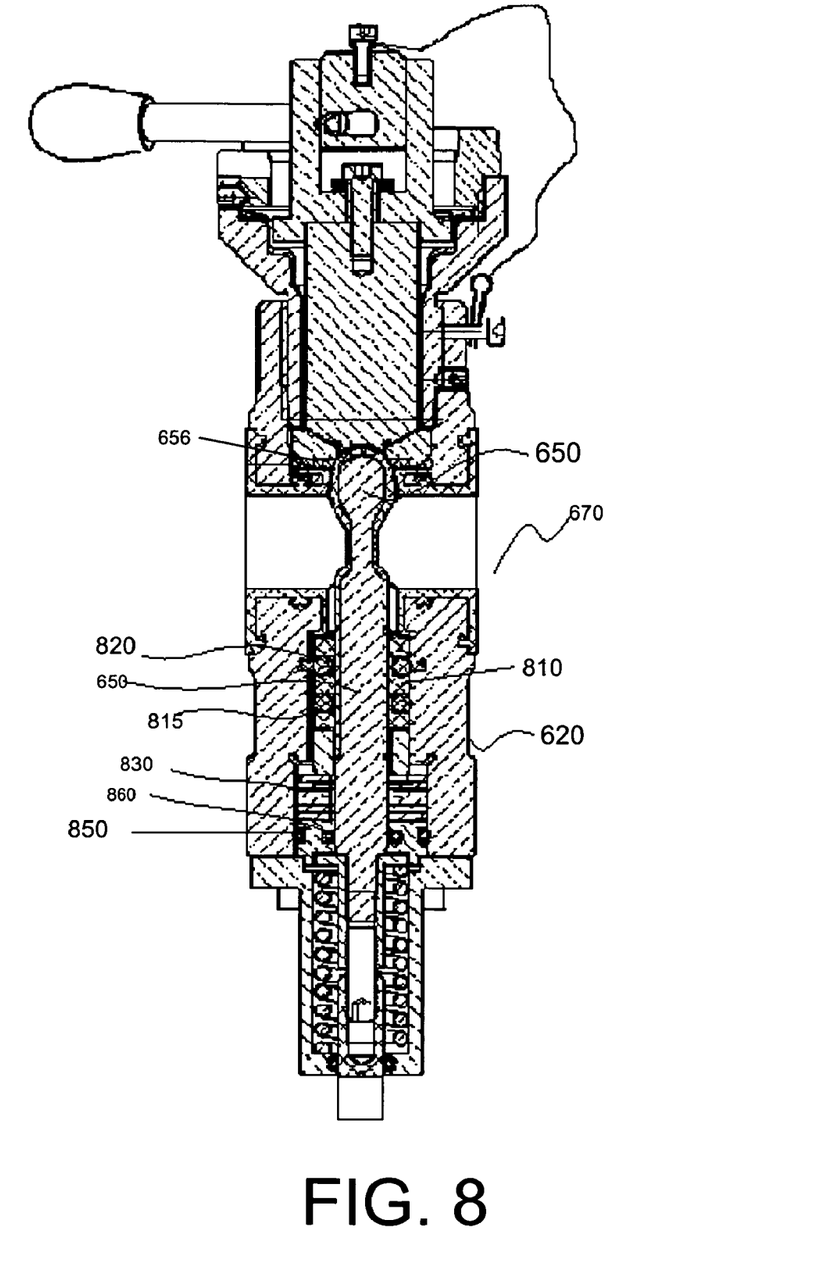
FIG. 8 is a detailed view of the sampling system utilizing a type of syringe shown generally in FIGS. 6 and 7.

FIG. 8 is a more detailed view of the sampling system utilizing a type of syringe shown in FIGS. 6 and 7 to better explain the positioning of the primary and secondary seal areas in this embodiment. As a preliminary matter, packing cartridge 810, O-ring 815 and O-ring 820 are identical to packing cartridge 410, O-ring 415 and O-ring 420. Thus, detailed descriptions of these references are omitted herein. Packing cartridge 810 is positioned around valve spindle 650 and provides a seal between spindle 650 and valve body 620. O-ring 815 and O-ring 820 positioned within cartridge 810 create a force exerted between valve unit body 620 and spindle 650. As described above, with reference to FIG. 5, cartridge 810 is a unitary valve member that is preloaded into valve unit body 620 with a centrally disposed channel 510 which receives valve spindle 650. O-ring 815 and O-ring 820 positioned within cartridge 810 create a force exerted between valve unit body 620 and spindle 650. Belleville washer 830 is positioned below cartridge 810. O-rings 850 and 860 are positioned below Belleville washer 830 where O-ring 850 exerts a force against spindle 650 via O-ring 860.

While the present invention has been disclosed with reference to certain preferred embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

What is claimed is:

1. A sampling device having a valve unit installed in a process pipeline for receiving a sample of process media flowing through said pipeline, said sampling device comprising:
   a valve unit body configured to house said valve unit, said valve unit having a valve port which in an open position supplies said sample of process media and in a closed position preventing said sample of process media from being extracted from said pipeline;
   a valve spindle disposed within said valve unit body, said valve spindle including a head portion, said spindle being spring biased in said closed position such that said head portion creates a seal with said valve port;

an operator connected to said valve spindle for moving said spindle from said open position to said closed position;

a packing cartridge positioned around said valve spindle, said cartridge having a first cut-out portion and an inner wall, said inner wall in contact with said valve spindle, said cartridge receiving a first O-ring received in said first cut-out portion for exerting a sealing force between said valve unit body and said spindle to prevent process flow from entering said valve unit body, said cartridge further comprising a lip portion located below said first cut-out portion, the lip portion further comprising an extension arm for wiping particles when said spindle moves with said valve unit body, said packing cartridge further comprising a second O-ring and a second cut-out portion for receiving said second O-ring to exert a sealing force between said valve unit body and said spindle to prevent process flow from entering said valve unit body; and a receptacle connected to said valve unit body configured to receive said sample media.

2. The sampling device in accordance with claim 1 further comprising a Belleville washer positioned above said packing cartridge, said Belleville washer allowing thermal expansion of said packing cartridge and said valve spindle.

3. The sampling device in accordance with claim 2 wherein said packing cartridge is a primary spindle seal, said sampling device further comprising:

a secondary spindle seal positioned above said Belleville washer, said secondary spindle seal having a third O-ring and a fourth O-ring positioned within a third cut-out portion and a fourth cut-out portion, respectively, said third O-ring exerting a sealing force between said valve unit body and said third O-ring, said third 0-ring positioned to exert a force against said spindle.

4. The sampling device in accordance with claim 1 wherein said cartridge further comprises a raised ring portion on said inner wall at said first cut-out portion, said raised ring portion lined with PTFE and in contact with said spindle to create a seal there between.

5. The sampling device in accordance with claim 1 wherein said valve unit body further comprises a sampling channel disposed between and connecting said receptacle and said valve port, said sampling channel configured to transport said sampling media from said valve port to said receptacle.

6. The sampling device in accordance with claim 5 wherein said valve unit body further comprises a sampling vent extending from said receptacle to an external surface of said valve body, said vent configured to discharge air from said receptacle when said receptacle receives said sample of process media.

7. The sampling device in accordance with claim 1 wherein said receptacle is a syringe.

8. The sampling device in accordance with claim 1 wherein said receptacle is a bottle detachably connected to said valve unit body.

9. The sampling device in accordance with claim 7 wherein said syringe is defined by a cylinder detachably connected to said valve unit body.

10. The sampling device in accordance with claim 9 further comprising a piston disposed within said cylinder, said piston configured to extract process media when said sampling device is in a vacuum pressure configuration.

11. A sampling device having a valve unit installed in a process pipeline for receiving a sample of process media flowing through said pipeline, said sampling device comprising:

a valve unit body configured to house said valve unit, said valve unit having a valve port which in an open position supplies said sample of process media and in a closed position prevents said sample of process media from being extracted from said pipeline;

a valve spindle disposed within said valve unit body and lined with PTFE, said valve spindle including a head portion, said spindle being spring biased in said closed position such that said head portion creates a seal with said valve port;

an operating lever connected to said valve spindle having a range of motion from said open position to said closed position; and a packing cartridge positioned around said valve spindle, said cartridge having a first cut-out portion and an inner wall, said inner wall lined with PTFE and in contact with said valve spindle, said cartridge receiving a first O-ring for exerting a sealing force between said valve unit body and said spindle to prevent process flow from entering said valve unit body, said packing cartridge further comprising a lip portion located adjacent said first cut-out portion, the lip portion including an extension arm engaged with said spindle for wiping particles when said spindle is lifted within said valve unit body;

wherein said packing cartridge further comprises a second O-ring and a second cut-out portion for receiving said second O-ring to exert a sealing force between said valve unit body and said spindle to prevent process flow from entering said valve unit body.

12. A sampling device having a valve unit installed in a process pipeline for receiving a sample of process media flowing through said pipeline, said sampling device comprising:

a valve unit body to house said valve unit, said valve unit having a valve port, said valve unit having an open position in which said sample of process media is receivable through said valve port, said valve unit having a closed position in which process media is prevented from being extracted from said pipeline through said valve port;

a valve spindle disposed within said valve unit body, said valve spindle including a head portion, said spindle being spring biased in said closed position to seal said head portion against said valve port;

an operating lever connected to said valve spindle, said operating lever movable from said open position to said closed position;

a primary spindle seal, a secondary spindle seal and a Belleville washer disposed between the primary and secondary spindle seals;

wherein the primary spindle seal comprises a packing cartridge positioned around said valve spindle, said packing cartridge comprising first and second O-rings received in first and second cut-out portions, said first and second 0-rings for exerting a sealing force between said valve unit body and said spindle to prevent process flow from entering said valve unit body, said packing; and wherein said secondary spindle seal comprises third and fourth O-rings disposed in third and fourth cut-outs, said third and fourth O-rings exerting a sealing force between said valve unit body and said spindle, said packing cartridge further comprising a lip portion having an extension arm engaged with said spindle for wiping away particles as said spindle is lifted within said valve unit body.

13. The sampling device of claim 12, wherein said packing cartridge has an inner wall, said inner wall having a raised ring corresponding to one of said first and second said cut-out portions.

14. The sampling device of claim 12, the extension arm having a downward curved radius for engaging said spindle.

15. The sampling device of claim 1, wherein the extension arm has a downward curved radius.

16. The sampling device of claim 15,
wherein said lip portion is located adjacent to said first cut-out portion.

17. The sampling device of claim 11, including a Belleville washer positioned adjacent to said packing cartridge, said washer allowing thermal expansion of said packing cartridge and said valve spindle.

18. The sampling device of claim 11, including a receptacle connected to said valve unit body and configured to receive said sample media.

19. The sampling device of claim 11, wherein the extension arm has a downward curved radius.

* * * * *